United States Patent [19]

Brion et al.

[11] Patent Number: 4,975,455
[45] Date of Patent: Dec. 4, 1990

[54] NEW HETEROAROTINOID COMPOUNDS

[75] Inventors: Jean-Daniel Brion, Saint-Leu la Foret; Guillaume Le Baut, Saint-Sebastien sur Loire; Patrick Ducrey, Rueil Malmaison; Sylvie Piessard-Robert, Nantes; Claude Cudennec, La Celle Saint-Cloud; Genevieve Seurre, Paris, all of France

[73] Assignee: Adir et Cie, Neuilly-sur-Seine, France

[21] Appl. No.: 336,224

[22] Filed: Apr. 11, 1989

[30] Foreign Application Priority Data

Apr. 13, 1988 [FR] France ................. 88 04870

[51] Int. Cl.⁵ ............... A61K 31/35; C07D 311/58
[52] U.S. Cl. ....................... 514/456; 549/408; 549/398; 549/60; 549/57; 548/525; 548/454; 546/269; 546/196; 544/332; 544/328; 544/322; 544/151; 544/62; 514/444; 514/443; 514/422; 514/414; 514/337; 514/320; 514/256; 514/231.5; 514/227.8
[58] Field of Search ............... 549/408, 398, 60, 57; 514/456, 443, 444, 422, 414, 337, 320, 256, 231.5, 227.8; 548/525, 454; 546/269, 196; 544/332, 328, 322, 151, 62

[56] References Cited

U.S. PATENT DOCUMENTS 4,808,597  2/1989  Hoffman et al. .............. 514/311
4,826,984  5/1989  Berlin et al. ................. 546/134

OTHER PUBLICATIONS

Suffness et al., J. Nat. Prod., 45, 1 (1982).

The Lancet, Apr. 16, 1983, pp. 860 through 863, "Nutrition: The Changing Scene".

*Primary Examiner*—Nicky Chan
*Attorney, Agent, or Firm*—Gordon W. Hueschen

[57] ABSTRACT

Compounds of general formula (I):

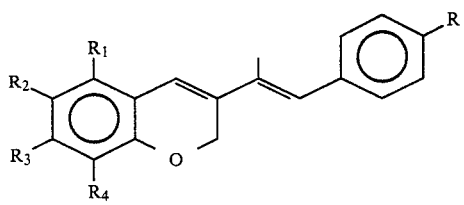

in which:

R denotes a hydrogen atom, a halogen atom or a hydroxy, lower alkyl, lower alkyloxy, carboxyl, (lower alkyloxy)carbonyl, (lower arylalkyloxy)carbonyl, aminocarbonyl, (lower mono- or dialkyl)aminocarbonyl or (lower arylalkyl)aminocarbonyl group, an aminocarbonyl group N-substituted with a heterocyclic radical, or a thio, (lower alkyl)thio, sulfonyl or (lower alkyl)sulfonyl group, $R_1$, $R_2$, $R_3$ and $R_4$, which may be identical or different, denote a hydrogen atom, a halogen atom or a lower alkyl, lower alkenyl, lower alkyloxy or lower alkenyloxy group, optionally substituted with one or more halogen atoms, their isomers, enantiomers, diastereoisomers and also, when R denotes a carboxyl, their addition salts with a pharmaceutically acceptable base and, when R contains a basic group, their addition salts with a pharmaceutically acceptable acid.

14 Claims, No Drawings

NEW HETEROAROTINOID COMPOUNDS

The present invention relates to new compounds endowed with anticancer properties belonging to the retinoid family, to a process for preparing them and to pharmaceutical compositions containing them.

Many substances of the retinoid family which are renowned for their anticancer properties are known U.S. Pat Nos. 4,054,589, 4,106,681, 4,137,246, 4,165,103, 4,169,100, 4,171,318, 4,224,244, BE 861,982, FR 2,556,348 and EP 111,124 describe compounds of the retinoid family in which the tetraene chain is attached to a monocyclic structure based on cyclohexene or benzene More especially, U.S. Pat. No. 4,105,681 describes etretinate, used in therapy, and whose anticancer properties are known at the present time.

Moreover, U.S. Pat. Nos. 4,588,750 and 4,326,055 describe molecules derived from retinoids, in which the tetraene chain is replaced by a β-methylstyryl group, the latter being attached to a bicyclic structure derived from tetrahydronaphthalene.

The needs of therapy demand the constant development of new anticancer agents, with the dual objective of obtaining molecules which are more active but, at the same time, less toxic.

The compounds of the present invention possess a novel structure consisting of a β-methylstyrene assembly attached to a bicyclic structure of the chromene type, which is to be found in many natural substances, the derivatives optionally being substituted on one or other ring.

The novelty of the structure of the compounds of the present invention makes it possible to obtain especially advantageous pharmacological properties, since the latter are, in the tests studied, superior to those of etretinate for many compounds : in addition, the compounds of the invention are of markedly lower toxicity than that of compounds having comparable activity known hitherto More especially, the subject of the present invention is compounds of general formula (I):

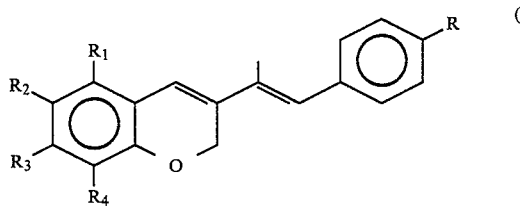

in which:
R denotes a hydrogen atom, a halogen atom or a hydroxy, lower alkyl, lower alkyloxy, carboxyl, (lower alkyloxy)carbonyl, (lower arylalkyloxy)carbonyl, aminocarbonyl, (lower mono- or dialkyl)aminocarbonyl or (lower arylalkyl)aminocarbonyl group, an aminocarbonyl group N-substituted with a heterocyclic radical, or a thio, (lower alkyl)thio, sulfonyl or (lower alkyl)sulfonyl group, $R_1$, $R_2$, $R_3$ and $R_4$, which may be identical or different, denote a hydrogen atom, a halogen atom or a lower alkyl, lower alkenyl, lower alkyloxy or lower alkenyloxy group, optionally substituted with one or more halogen atoms, their isomers, enantiomers, diastereoisomers and also, when R denotes a carboxyl, their addition salts with a pharmaceutically acceptable base and, when R contains a basic group, their addition salts with a pharmaceutically acceptable acid.

Among bases capable of salifying the compounds of formula (I) in which R denotes a carboxyl group, there may be mentioned, by way of example, sodium hydroxide, potassium hydroxide, calcium hydroxide or aluminum hydroxide, alkali metal or alkaline-earth metal carbonates, or organic bases such as triethylamine, benzylamine, diethanolamine, tert-butylamine, dicyclohexylamine, arginine, and the like.

Among acids capable of salifying the compounds of formula (I), there may be mentioned, by way of a non-limiting example, hydrochloric, sulfuric, tartaric, maleic, fumaric, oxalic, methanesulfonic and camphoric acids, and the like.

Lower alkyl, lower alkyloxy, alkenyl and lower alkenyloxy radicals are understood to mean linear or branched groups comprising between 1 and 6 carbon atoms.

Heterocyclic radical is understood to mean a saturated or unsaturated mono- or bicyclic system including one or more heteroatoms such as sulfur, oxygen or nitrogen in a carbon skeleton. There may be menthiophene, pyrrole, benzothiophene, benzopyrrole, pyrimidine, piperidine, morpholine, thiomorpholine, pyrrolidine and the like.

The present invention also encompasses a process for preparing the compounds of formula (I), wherein a compound of formula (II):

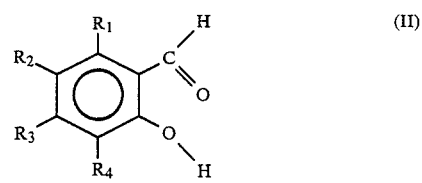

in which $R_1$, $R_2$, $R_3$ and $R_4$ have the same meaning as in the formula (I), is condensed by heating under reflux of the solvent with 3-oxo-1-butene of formula (III):

in the presence of an alkaline agent preferably chosen from alkali metal and alkaline-earth metal carbonates, or organic bases such as, for example, triethylamine or pyridine, or a mixture consisting of an alkali metal carbonate or alkaline-earth metal carbonate and an organic base, in a polar solvent preferably chosen from 2-butanone, dimethylformamide, acetone and dimethyl sulfoxide, to lead, after cooling and, where appropriate, evaporation of the reaction medium, taking up with water to which an alkaline agent such as sodium hydroxide has been added where appropriate, extraction with a suitable organic solvent such as diethyl ether, dichloromethane or chloroform, washing of the organic phase, evaporation of the solvent and purification of the residue by crystallization or distillation or chromatography on a silica or alumina column, to a compound of formula (IV):

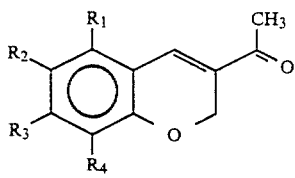

in which $R_1$, $R_2$, $R_3$ and $R_4$ have the same meaning as in formula (I), which compound after dissolution in a suitable organic solvent preferably chosen from lower aliphatic alcohols, is subjected, preferably in the presence of an alkaline agent such as sodium hydroxide, to catalytic hydrogenation preferably with an alkali metal mixed hydride such as sodium borohydride, to lead, after evaporation of the reaction medium where appropriate, extraction with a suitable organic solvent such as diethyl ether, methylene chloride or chloroform, washing, then evaporation of the organic phase and purification, to a compound of formula (V):

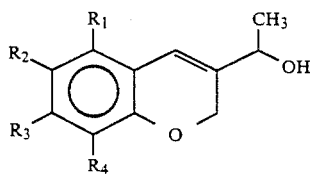

in which $R_1$, $R_2$, $R_3$ and $R_4$ have the same meaning as above, which compound is subjected to the action of a triphenylphosphonium salt in a solvent preferably chosen from lower aliphatic alcohols, at room temperature and with stirring, to lead, after evaporation of the solvent and purification by chromatography on silica gel or by crystallization in a solvent or a mixture of suitable solvents, to a compound of formula (VI):

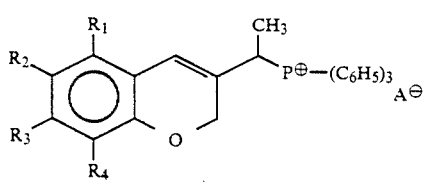

in which $R_1$, $R_2$, $R_3$ and $R_4$ have the same definition as in formula (I), and A- denotes the anion of a hydracid, which, after being suspended in an organic solvent, is treated with a solution of n-butyllithium in hexane, preferably at room temperature, and then treated with a compound of formula (VII):

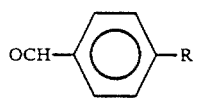

in which R has the same meaning as in formula (I), preferably at room temperature, to lead, after dilution in water or removal of the solvent, extraction with an organic solvent chosen from diethyl ether, diisopropyl ether, chloroform and methylene chloride, and purification by chromatography on a silica column, to a compound of formula (I), which can, if so desired, either, when R denotes a carboxyl group, be salified with a pharmaceutically acceptable base, or, when R contains a basic group, be salified with a pharmaceutically acceptable acid, or be separated into its isomers, diastereoisomers or enantiomers by a technique of crystallization or chromatography and then, if so desired, when R denotes a carboxyl group, be salified with a pharmaceutically acceptable base, or, when R contains a basic group, be salified with a pharmaceutically acceptable acid.

A special case of the compounds of formula (I) of the present invention relates to compounds of formula (I/A):

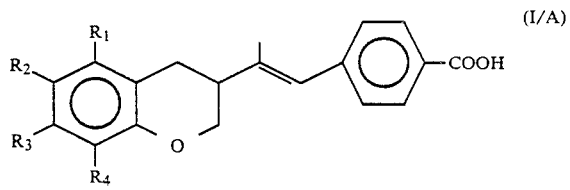

for which $R_1$, $R_2$, $R_3$ and $R_4$ have the same meaning as above.

The compounds of the formula (1/A) may be obtained by simple alkaline hydrolysis of derivatives of formula (I/B):

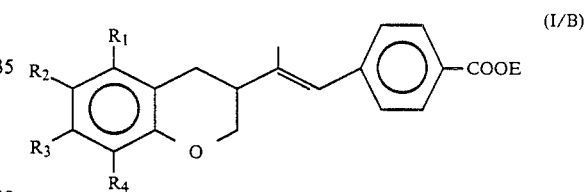

a special case of the compounds of formula (I) for which R denotes a group COOE, in which E denotes a lower alkyl group and $R_1$, $R_2$, $R_3$ and $R_4$ have the same meaning as above, followed, if necessary, by the separation of the isomers, enantiomers or diastereoisomers and, where appropriate, salification with a pharmaceutically acceptable base.

The compounds of formula (I) possess very advantageous pharmacological properties. They inhibit more strongly than etretinate the growth of L 1210 line in mice and, an especially advantageous factor for their use in therapy, do not appear to cause excess-vitamin A toxicity, which is induced by etretinate and symptoms of which are rapid weight loss, alopecia and bone weakening.

The compounds according to the present invention hence find a use in therapy as antitumor agents, for the treatment or prophylaxis of benign or malignant neoplasms, as well as in the traditional indications for retinoids, such as skin disorders (acne, psoriasis), as well as degenerative disorders and/or inflammation of the mucosae.

The subject of the present invention is also the pharmaceutical compositions containing the products of the formula (I), or one of their addition salts with a pharmaceutically acceptable base or acid when R denotes a salifiable group, alone or in combination with one or more pharmaceutically acceptable, non-toxic, inert vehicles or excipients.

Among the pharmaceutical compositions according to the invention, there may be mentioned, more especially, those which are suitable for oral, parenteral, nasal, rectal, perlingual, ocular or respiratory administration, and in particular, tablets, simple or sugar-coated, sublingual tablets, sachets, packs, hard gelatin capsules, preparations to be dissolved under the tongue, bars, suppositories, creams, ointments, skin gels, injectable preparations or preparations to be swallowed, aerosols, eye or nose drops, and the like.

The appropriate dosage varies according to the patient's age and weight, the administration route and the nature of the therapeutic indication and of any associated treatments, and ranges between 0.1 and 200 mg per day.

The examples which follow illustrate the invention but in no way limit the latter.

The nuclear magnetic resonance spectra, except where otherwise stated, are produced in chloroform with an apparatus at 60 MHz, using TMS as internal reference. The shifts are expressed in ppm.

The preparations included below relate to compounds . which do not form part of the present invention, but which are useful as intermediates during the synthesis of the derivatives of the invention.

PREPARATION 1

ETHYL 4-FORMYLBENZOATE

STAGE A: 4-(HYDROXYMETHYL)BENZOIC ACID

A solution of 3.68 g (92.3 mmol) of sodium borohydride, dissolved in 30 ml of water to which 5 ml of 5N NaOH have been added, is added dropwise and with stirring to a solution of 13.86 g (92.3 mmol) of 4-formylbenzoic acid in 200 ml of absolute ethanol. The reaction medium is left thus for 5 hours with stirring at room temperature. The ethanol is then removed by evaporation under vacuum and the residue is taken up with water and then acidified with 5N hydrochloric acid: the precipitate obtained is separated by filtration on a sinter.

On the one hand the filtrate is extracted with ethyl ether (3×150 ml), and on the other hand the precipitate is exhaustively extracted with ethyl ether in the heated state. Evaporation of the organic phases yields 10.5 g of the expected product.

Overall yield: 75%
Melting point: 178° C.

STAGE B: ETHYL 4-(HYDROXYMETHYL)BENZOATE 4 g (26.3 mmol) of 4-(hydroxymethyl)benzoic acid in 1,000 ml of absolute ethanol are heated under reflux of the solvent for 15 hours in the presence of approximately 1 g of concentrated sulfuric acid. The ethyl alcohol is then evaporated off and the residue taken up with water. After extraction of the aqueous phase with 3×100 ml of ethyl ether, the organic phases are washed to neutrality with saturated sodium hydrogen carbonate solution. After removal of the solvent, 4.56 g of a yellow oil, which soon crystallizes, remains.

Overall yield: 96%

STAGE C: ETHYL 4-FORMYLBENZOATE 24.1 g (0.277 mmol) of manganese dioxide are added with stirring and at room temperature to a solution of 2.5 g (13.9 mmol) of ethyl 4-(hydroxymethyl)benzoate in an n-hexane/carbon tetrachloride (50 ml : 30 ml) mixture. After half an hour of stirring, the reaction is complete. After filtration of the reaction medium and removal of the solvents under vacuum, 1.76 g of a yellow oil which gives a single spot in TLC are obtained. A crystallization in isopropyl ether yields a white solid.

Overall yield: 71%
Melting point: 157° C.

PREPARATION 2

METHYL 4-FORMYLBENZOATE

By replacing ethanol with methanol in Preparation 1, stage B, the expected product is obtained.

PREPARATION 3

N-ETHYL-4-FORMYLBENZAMIDE

This compound is obtained in 3 stages from 4-formylbenzoic acid, which is subjected to the action of thionyl chloride to produce the corresponding acid chloride, which is treated with ethylamine in a suitable organic solvent such as benzene, for example, to produce the expected product Overall yield 25%
Melting point: 100° C.

PREPARATION 4

ETHYL 4-FORMYLPHENYL SULFONE

This compound is obtained in 4 stages from para-bromothiophenol, which is subjected to the action of an ethylating agent such as ethyl iodide in the presence of sodium ethylate to produce 4-bromo-S-ethylthiophenol, which is treated with magnesium in a solvent such as tetrahydrofuran or ethyl or diisopropyl ether and subjected to the action of an acid to produce para-(ethylthio)benzaldehyde which, under the action of oxidizing agents, enables the expected product to be obtained.

Melting point: 114° C.

PREPARATION 5

5,6 TM DIMETHYL-2-HYDROXY-4-METHOXYBENZALDEHYDE

STAGE A: 1,5-(2,3-DIMETHYLPHENYL) DIACETATE 27 g (0.192 mmol) of dimedone and 300 ml of acetic anhydride are introduced in a round-bottomed flask equipped with a condenser and a nitrogen inlet, and 12 ml of concentrated sulfuric acid are then introduced dropwise and with stirring; a distinct warming of the reaction medium is observed The reaction is then heated under reflux for one hour under nitrogen After being cooled, the reaction medium is cast into an ice-/water mixture and stirred thus for 40 minutes The aqueous phase is then extracted with 4×250 ml of ether. After neutralization with saturated sodium hydrogen carbonate solution and washing with saturated brine solution, the ether phase is dried over sodium sulfate. Removal of the solvent yields an oily residue (21 g), which is distilled under vacuum.

Yield: 49%.

STAGE B: 2,3-DIMETHYL-5-HYDROXYPHENOL (M. S. KABLAOUI, J. ORG. CHEM. 1974, 39 (25) 3696)

13.30 g (60 mmol) of 1,5-(2,3-dimethylphenyl) diacetate are saponified after 2 hours, heating under reflux with a sodium hydroxide solution [6 g (0.15 mmol) of NaOH in 50 ml of water]. After cooling, and acidification of the solution with 2.5N hydrochloric acid, the reaction medium is extracted with 3×250 ml of ethyl ether. The organic phase is washed with water and the ethyl ether then removed. The oily residue crystallizes. After the crystals are taken up with benzene and separation is carried out by filtration on a sinter, 4.45 g of a white solid are obtained.
Yield: 53%
Melting point: 135°–136° C.

STAGE C: 2,4-DIHYDROXY-5,6-DIMETHYLBENZALDEHYDE (A. ROBERTSON, W. B. WHALLEY, J. CHEM. SOC., 1949, 3033)

4.450 g (32 mmol) of 2,3-dimethyl-5-hydroxyphenol are dissolved in 100 ml of anhydrous ethyl ether in a round-bottomed flask equipped with a gas inlet, a thermometer and a condenser (the outflow gases being trapped by 3 successive bubblers: $H_2SO_4$, saturated $KMnO_4$ solution, 3N NaOH). After 5.635 g (48 mmol) of zinc cyanide have been added, a stream of gaseous hydrochloric acid is passed through for 2 hours with stirring at room temperature. A copious precipitate appears, increasing with the passage of time. At the end of the operation, a powerful stream of nitrogen is passed through the reaction medium. The insoluble matter is separated by filtration and dissolved in boiling water. After cooling, the aldehyde precipitates. After filtration, the crystals are washed with water and dried.
Yield: 71%
Melting point: 196° C.

STAGE D: 5,6-DIMETHYL-2-HYDROXY-4-METHOXYBENZ ALDEHYDE 23 g (0.138 mmol) of 2,4-dihydroxy-5,6-dimethylbenzaldehyde are dissolved in 200 ml of anhydrous acetone in a round-bottomed flask. 38 g (0.276 mmol) of dry potassium carbonate and 9.50 ml (0.152 mmol) of methyl iodide are added successively to the solution. The reaction medium is heated under reflux for 20 hours. After the mixture has cooled and the insoluble matter filtered off, the acetone is removed by evaporation under vacuum. The residue is taken up with water and extracted with 3×150 ml of ethyl ether and then with 2×100 ml of dichloromethane. After evaporation of the organic solvents, 5,6-dimethyl-2-hydroxy-4-methoxybenzaldehyde crystallizes. Purification after chromatography on a column of silica gel yields 24.8 g.
Yield: 83%
Melting point: 121° C.

EXAMPLE 1: 3-(1-PHENYLPROPEN-2-YL)-2H-CHROMENE

STAGE A: 3-ACETYL-2H-CHROMENE 1.22 g (10 mmol) of salicylaldehyde together with 0.66 g (10 mmol) of 3-oxo-1-butene are added at room temperature to a suspension of 0.14 g (1 mmol) of potassium carbonate in 50 ml of 2 TM butanone. The mixture is brought to reflux with stirring and this temperature is maintained for 4 hours. The reaction medium is evaporated on a water bath under vacuum and the residue taken up with 100 ml of water and extracted three times with 75 ml of diethyl ether. The organic phases are combined, washed to neutrality with saturated aqueous sodium chloride solution, dried over sodium sulfate and filtered, the filtrate is evaporated on a water bath under vacuum and the product recrystallized in hexane
Yield: 57%.

STAGE B: 3-(1-HYDROXYETHYL)-2H-CHROMENE 1.75 g (10 mmol) of 3-acetyl-2H-chromene, obtained in the preceding stage, are dissolved in 50 ml of ethanol. A solution of 0.38 g (10 mmol) of sodium borohydride in 5 ml of aqueous sodium hydroxide solution is added in a single portion with magnetic stirring. Stirring is maintained for 2 hours and the solvent mixture is then evaporated. The residue is taken up with 50 ml of water and extracted three times with 50 ml of diethyl ether. The ethereal solution is washed with saturated aqueous sodium chloride solution until the washing liquors are neutral, the organic phase is dried and evaporated and the product thereby obtained is used in the next phase.
Yield: 95%.

STAGE C: [1-(2H-CHROMEN-3-YL)ETHYL]TRIPHENYLPHOSPHONIUM BROMIDE 1.77 g (10 mmol) of 3-(1-hydroxyethyl)-2H-chromene, obtained in the preceding stage, and 3.43 g (10 mmol) of triphenylphosphonium hydrobromide in 80 ml of methanol are placed under a nitrogen atmosphere at room temperature. The mixture is stirred for 96 hours. The methanol is removed by evaporation and the residue obtained chromatographed on a column of silica gel (70–230 mesh), using a methylene chloride/ethanol (95:5 v/v) mixture as elution solvent, and the product is crystallized in a benzene/acetone solvent mixture.
Yield: 85%
Melting point: 198° C.

STAGE D: 3-(1-PHENYLPROPEN-2-YL)-2H-CHROMENE 5 g (10 mmol) of [1-(2H-chromen-3-yl)ethyl]triphenylphosphonium bromide, obtained in the preceding stage, are suspended in 30 ml of tetrahydrofuran. 6.9 ml of a 1.6M solution of n-butyllithium in hexane are added at room temperature under a nitrogen atmosphere and with magnetic stirring. The reactants are left in contact for 10 minutes and a solution of 1.06 g of benzaldehyde (10 mmol) in 50 ml of TMF is then added in the course of 20 minutes. Stirring is continued for 4 hours. The reaction medium is diluted with 75 ml of water and extracted 3 times with 75 ml of diethyl ether. The organic phases are combined, and washed to neutrality with saturated aqueous sodium chloride solution. The organic phase is dried and evaporated and the residue purified by two preparative chromatographic runs on a column of silica gel.
1/SiO₂ 70–230 mesh
2/SiO₂ 200–400 mesh
An oil is thereby obtained, a mixture of Z and E isomers which are purified by fractional crystallization.
Yield: 70%
Melting point: oil

| Elemental analysis: | | |
|---|---|---|
| Calculated: | C: 87.06 | H: 6.49 |
| Found: | C: 86.84 | H: 6.36 |

Spectral characteristics: Infrared (cm$^{-1}$): 1600, 1580, 1480, 1460, 1220, 750, 700

| Nuclear magnetic resonance (60 MHz): | |
|---|---|
| δ = 2.05 and 2.15 | 3H singlet CH$_3$ |
| δ = 4.85 and 5.20 | 2H singlet chromene CH$_2$ |
| δ = 6.45 − 7.60 | complex 11H ethylenic and aromatic. |

EXAMPLE 2:
3-(1-PHENYLPROPEN-2-YL)-2H-CHROMENE E,E,E ISOMER

The procedure is as in Example 1, and the E isomer is separated from the mixture of isomers obtained in Example 1, stage D.
Yield: 10%

| Elemental analysis: | | |
|---|---|---|
| Calculated: | C: 87.06 | H: 6.49 |
| Found: | C: 86.30 | H: 6.50 |

Spectral characteristics: Infrared: 1600, 1580, 1480, 1460, 1220, 750, 700

| Nuclear magnetic resonance (solvent CDCl$_3$): | |
|---|---|
| δ = 2.15 ppm | 3H singlet CH$_3$ |
| δ = 5.20 ppm | 2H singlet chromene CH$_2$ |
| δ = 6.45 to 7.60 ppm | 11H ethylenic and aromatic. |

EXAMPLES 3 TO 19

Using the procedure described in Examples 1 or 2, depending on whether or not it is desired to separate the E,E,E isomer from the mixture, the following are obtained:

By replacing benzaldehyde in stage D by 4-formylbenzoic acid methyl ester (obtained in Preparation 2), methyl 4-[2-(2H-chromen-3-yl)propenyl]benzoates are obtained.

By replacing benzaldehyde in stage D by 4-formylbenzoic acid ethyl ester (obtained in Preparation 1), ethyl 4-[2-(2H-chromen-3-yl)propenyl]benzoates are obtained.

By replacing benzaldehyde in stage D by N-ethyl-4-formylbenzamide (obtained in Preparation 3), N-ethyl-4-[2-(2H-chromen-3-yl)propenyl]benzamides are obtained.

By replacing benzaldehyde in stage D by ethyl 4-formylphenyl sulfone (obtained in Preparation 4), ethyl 4-[2-(2H-chromen-3-yl)propenyl]phenyl sulfones are obtained.

It is also possible to use the procedure described in Examples 1 and 2, replacing:

* in stage A of Example 1, salicylaldehyde by a substituted salicylaldehyde of general formula (II/1)

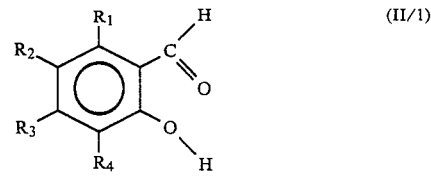

a special case of the compounds of formula (II) in which $R_1$, $R_2$, $R_3$, $R_4$ have the same meaning as in the formula (I) excluding the case where $R_1$, $R_2$, $R_3$ and $R_4$ simultaneously denote a hydrogen atom.

* in stage A of Example 1, salicylaldehyde by a derivative of the formula (II/1), and in stage D benzaldehyde by:
  either 4-formylbenzoic acid methyl ester,
  or 4-formylbenzoic acid ethyl ester,
  or N-ethyl-4-formylbenzamide,
  or ethyl 4-formylphenyl sulfone.

Tables A show the data relating to the synthesis of Examples 3 to 19.

Table A1 shows more especially the characteristics of the 3-acetylchromenes [compounds of formula (IV)].

Table B shows the physicochemical characteristics of Examples 3 to 19.

TABLE A

| EX N° | R$_1$ | R$_2$ | R$_3$ | R$_4$ | R | Stereo-chemistry | STAGE A T1 | STAGE A Yld (%) | STAGE B Yld (%) | STAGE C Yld (%) | STAGE C M.p. (°C.)* | STAGE D T2 (n) | STAGE D Yld (%) |
|---|---|---|---|---|---|---|---|---|---|---|---|---|---|
| 3 | H | Cl | H | CH$_3$ | H | E + Z | 4 | 50 | 93 | 58 | 172 | 6 | 75 |
| 4 | H | CH$_3$ | H | CH$_3$ | H | E + Z | 1.5 | 81 | 86 | 68 | 164 | 6 | 48 |
| 5 | CH$_3$ | CH$_3$ | OCH$_3$ | H | H | E | 1.5 | 25 | | 57 | 134 | 6 | 12 |
| 6 | H | H | H | H | COOCH$_3$ | E | 4 | 57 | 95 | 85 | 198 | 24 | 22 |
| 7 | H | Cl | H | CH$_3$ | COOCH$_3$ | E | 4 | 50 | 93 | 58 | 172 | 24 | 20 |
| 8 | H | Cl | H | Cl | COOCH$_3$ | E | 4 | 20 | 87 | 46 | 193 | 24 | 18 |
| 9 | CH$_3$ | CH$_3$ | OCH$_3$ | H | COOCH$_3$ | E | 1.5 | 25 | | 57 | 134 | 18 | 30 |
| 10 | H | H | H | H | COOC$_2$H$_5$ | E | 4 | 57 | 95 | 85 | 198 | 24 | 24 |
| 11 | H | Cl | H | CH$_3$ | COOC$_2$H$_5$ | E | 4 | 50 | 93 | 58 | 172 | 24 | 16 |
| 12 | H | CH$_3$ | H | CH$_3$ | COOC$_2$H$_5$ | E + Z | 1.5 | 81 | 86 | 68 | 164 | 18 | 70 |
| 13 | H | H | H | H | CONHC$_2$H$_5$ | E | 4 | 57 | 95 | 85 | 198 | 18 | 23 |
| 14 | H | Cl | H | CH$_3$ | CONHC$_2$H$_5$ | E | 4 | 50 | 93 | 58 | 172 | 18 | 42 |
| 15 | H | CH$_3$ | H | CH$_3$ | CONHC$_2$H$_5$ | E | 1.5 | 81 | 86 | 68 | 164 | 18 | 56 |
| 16 | H | H | H | H | SO$_2$C$_2$H$_5$ | E | 4 | 57 | 95 | 85 | 198 | 84 | 14 |
| 17 | H | Cl | H | CH$_3$ | SO$_2$C$_2$H$_5$ | E + Z | 4 | 57 | 93 | 58 | 172 | 6 | 41 |
| 18 | H | CH$_3$ | H | CH$_3$ | SO$_2$C$_2$H$_5$ | E + Z | 1.5 | 81 | 86 | 68 | 164 | 4 | 36 |
| 19 | H | Cl | H | Cl | SO$_2$C$_2$H$_5$ | E | 4 | 50 | 93 | 46 | 193 | 24 | 14 |

*Melting point of the phosphonium salt obtained at the end of stage C
T1 = refluxing time
T2 = reaction time.

TABLE A1
PURIFICATION OF THE 3-ACETYL-2H-CHROMENES

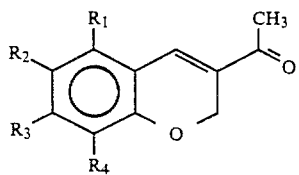

| $R_1$ | $R_2$ | $R_3$ | $R_4$ | M.p. °C. | PURIFICATION METHOD |
|---|---|---|---|---|---|
| H | H | H | H | 58–60 | recryst. (hexane) |
| H | OCH$_3$ | H | H | 59 | recryst. (isopropyl ether) |
| H | H | OCH$_3$ | H | 72 (yellow) | chrom. on column of silica gel (200–400 mesh); eluent: CH$_2$Cl$_2$ |
| H | CH$_3$ | H | CH$_3$ | 41–42 (yellow) | chrom. on column of silica gel (70–230 mesh); eluent: CH$_2$Cl$_2$ |
| H | Cl | H | CH$_3$ | 78–79 (yellow) | chrom. on column of silica gel (70–230 mesh); eluent: CH$_2$Cl$_2$ then recryst. (isopropyl ether/petroleum ether) |
| H | Cl | H | Cl | 108 (yellow) | chrom. on column of silica gel (70–230 mesh); eluent: CH$_2$Cl$_2$ |
| CH$_3$ | CH$_3$ | OCH$_3$ | H | 110 (yellow) | chrom. on column of alumina and recryst. in ethanol |

TABLE B
PHYSICOCHEMICAL CHARACTERISTICS OF EXAMPLES 3 TO 18

| Ex No | M.p. (°C.) | ELEMENTAL ANALYSIS CALCULATED | FOUND | INFRARED (cm$^{-1}$) | NUCLEAR MAGNETIC RESONANCE* (δ) ppm |
|---|---|---|---|---|---|
| 3 | Oil | C 76.89<br>H 5.77 | C 76.91<br>H 5.80 | 1600, 1580, 1460 1200 750, 690 | 2.15: s; 3H; CH$_3$ (chromene)<br>2.25; s; 3H; CH$_3$ (ethylene)<br>5.20; b.s.; 2H; chromene-6.65. s, 1H ethylene<br>6.85–7.55: 8H: aromatic + 1H chromene |
| 4 | Oil | | | | |
| 5 | 97° C. | | | | |
| 6 | 115° C. | C 78.43<br>H 5.88 | C 78.33<br>H 6.01 | 1720, 1610, 1120 760 | 2.25: s; 3H: CH$_3$ (ethylene).4.00 s; 3H; ester<br>5.20; b.s.: 2H chromene; 6.60: b.s.; 1H ethylene<br>6.65–7.35; c; 5H; ar and chromene<br>7.85–8.30; 4H; ar (AA'BB') |
| 7 | 135° C. | C 69.32<br>H 5.54 | C 69.28<br>H 5.50 | 1725, 1610, 1155 760 | 2.15: s; 3H: CH$_3$ (ethylene)<br>2.20 s; 3H: CH$_3$: chromene<br>3.90: s; 3H: CH$_3$ (ester)<br>5.10 b.s; 2H; CH$_2$ chromene<br>6.45; b.s.: 1H; ethylenic H<br>6.55; b.s.: 1H; chromene H$_4$<br>7.20–8.10; 4H: AA'BB' ar and 2H ar |
| 8 | 172° C. | C 64.01<br>H 4.30 | C 63.46<br>H 4.49 | 1730, 1610, 1120 | 2.15; s; 3H: CH$_3$ (ethylene)-3.95; s; 3H (ester)<br>5.25; b.s.; 2H; CH$_2$ (chromene);<br>6.65–7.05 (3H, c H$_4$, H$_5$ and ethylene H)<br>7.40–8.10; 5H: AA'BB' and H$_7$ |
| 9 | 166° C. | C 75.80<br>H 6.64 | C 75.36<br>H 6.68 | 1710, 1590, 1280 | 2.15 s; 3H: CH$_3$ (ethylene);<br>2.20 and 2.35; 2s; 2 × CH$_3$ (chromene)<br>3.85 s; 3H; OCH$_3$; 3.95; s; 3H; ester CH$_3$<br>5.05; b.s.; 2H; H$_2$; chromene<br>6.35–8.25 (7H, complex, 4H arom, 2H chromene 1H ethylenic) |
| 10 | 120° C. | C 78.73<br>H 6.29 | C 78.68<br>H 6.18 | 1730, 1620 | 1.41; t; 3H; CH$_2$—CH$_3$; 2.15.b.s. 3H; ethylene CH$_3$<br>4.35; q; 2H; OCH$_2$—CH$_3$; 5.1.b.s.; 2H; CH$_2$; chromene<br>6.45; 1H; b.s.; 2H; H ethylene;<br>6.6–8.10 c; 9H; aromatic t 1H chromene |
| 11 | 127° C. | C 70.49<br>H 5.63 | C 70.42<br>H 5.10 | | 1.40; t; 3H—CH$_2$—CH$_3$; 2.10; s; 3H; CH$_3$ chromene<br>2.20; b.s.; 3H; CH$_3$ ethylene<br>4.40; q; 2H; COOCH$_2$CH$_3$<br>5.15; b.s.; 2H; H$_2$ chromene, 6.50; b.s.; 1H ethylene<br>6.60–8.20; complex: 7H; H aromatic + chromene |
| 12 | | C 79.28<br>H 6.94 | C 79.01<br>H 6.83 | | 1.50 and 1.70; 3H; 2t; COOCH$_2$CH$_3$<br>2.15 and 2.45; 9H multiplet ethyl CH$_3$ and chromene 2CH$_3$<br>4.50; 2H; q; COOCH$_2$—CH$_3$<br>4.90 and 5.20; 2H; 2 b.s.; H$_2$<br>6.60 and 6.75; 1H; 2 b.s.; ethyl H<br>6.85–8.30; 7H; multiplet H$_4$, H$_5$, H$_7$ and 4H ar |
| 13 | 187° C. | C 78.97<br>H 6.63<br>N 4.38 | C 78.82<br>H 6.60<br>N 4.26 | | 1.25; (t); 3H; NH—CH$_2$—CH$_3$; J=7Hz; 2.15 b.s.; 3H; CH$_3$<br>3.50; q 2H; NH—CH$_2$—CH$_3$; J=7Hz; 5.15 b.s.; 2H H$_2$<br>6.10–7.95 complex; 11H; ethylene H, H$_4$, H$_5$, H$_6$, H$_7$, H$_8$, A ar AA'BB', NH |
| 14 | 166° C. | C 71.83<br>H 6.03 | C 71.75<br>H 6.11 | | 1.25; t 3H; NH—CH$_2$—CH$_3$<br>2.15 b.s. 3H CH$_3$; ethylene |

TABLE B-continued

PHYSICOCHEMICAL CHARACTERISTICS OF EXAMPLES 3 TO 18

| Ex No | M.p. (°C.) | ELEMENTAL ANALYSIS CALCULATED | FOUND | SPECTROMETRY INFRARED (cm$^{-1}$) | NUCLEAR MAGNETIC RESONANCE* (δ) ppm |
|---|---|---|---|---|---|
| | | N 3.81 | N 3.85 | | 2.25; s; 3H; CH$_3$ (8) chromene; 3.55; q; 2H; NH—C$\underline{H_2}$—CH$_3$ 5.15; b.s.; 2H; H-2 chromene 6.20 mult.; 1H; N$\underline{H}$ 6.45–8.00; 8H; ethylene H + chromene H + aromatic H |
| 15 | 152° C. | C 79.51 | C 79.47 | | 1.30; t; 3H; NH—CH$_2$—C$\underline{H_3}$; 2.15 b.s. 3H; CH$_3$ ethylene |
| | | N 7.29 | H 7.37 | | 2.25, 2.30: 2s 2 × 3H (CH$_3$ and chromene CH$_3$) |
| | | H 4.03 | N 4.06 | | 6.25 c; 1H; N$\underline{H}$, 6.50–8.15 (c, 8H; ethylene H + chromene H + arom H) |
| 16 | 149° C. | C 70.56 | C 70.64 | | Solvent DMSO d6 |
| | | H 5.92 | H 5.96 | | 1.10; t; 3H; CH$_3$ (C$_2$H$_5$) J=7H$_2$-2.20 s; 3H; CH$_3$; ethyl 3.30; q; 2H; CH$_2$ (C$_2$H$_5$); J=7H$_2$-5.15 b.s.; 2H; chromene H$_2$ 6.50–8.10 c; 10 H; ethyl and aromatic |
| 17 | | C 64.85 | C 64.12 | | 1.25 and 1.75; t; 3H; SO$_2$CH$_2$C$\underline{H_3}$ |
| | | H 5.44 | H 5.80 | | 2.10; b.s.; 3H; CH$_3$ (ethylenic) 2.25; s; 3H; CH$_3$ (chromenyl) 3.15; q; 2H; SO$_2$CH$_2$CH$_3$; 4.90 and 5.15; 2b.s.; 2H; H$_2$ 6.40–8.20; multiplet; 8H; ethyl and aromatic H |
| 18 | | C 70.00 | C 70.28 | | 1.25 and 1.85; 2t; 3H SO$_2$CH$_2$CH$_3$ |
| | | H 6.67 | H 6.23 | | 2.15: b.s.; 3H CH$_3$ (ethylenic) 2.20: s; 6H; 2CH$_3$ (chromene) 3.10: q; 2H; SO$_2$—CH$_2$—CH$_3$; 4.80–5.10: 2H, 2 b.s.; H$_2$ 6.40–8.10: 8H, c, ethylene H and 4 H ar and H$_4$, H$_5$, H$_7$ | s = singlet;
b.s.: broad signal

EXAMPLE 20:
3 TM (1 TM PHENYLPROPEN-2-YL)-6-METHOXY-2H-CHROMENE

STAGE A:
6-METHOXY-3-ACETYL-2H-CHROMENE 1.52 g (10 mmol) of 2-hydroxy TM 5-methoxybenzaldehyde, 0.66 g of 3-oxo-1-butene and 1.4 g (10 mmol) of potassium carbonate are added at room temperature and with magnetic stirring to 40 ml of 2-butanone. The mixture is brought to reflux with stirring and this temperature is maintained for 2 hours. After being cooled, the reaction medium is poured into 100 ml of water and extracted 3 times with 100 ml of diethyl ether. The organic phases are combined, washed to neutrality with saturated aqueous sodium chloride solution and dried over sodium sulfate, and the organic phase is evaporated on a water bath under vacuum and the product recrystallized.

Yield: 77%

STAGES B TO D

The procedure is as in Example 1, 3-acetyl-2H-chromene being replaced by 6-methoxy-3-acetyl-2H-chromene.

EXAMPLES 21 TO 24

Using the procedure described in Example 20, by replacing benzaldehyde in stage D by:

4-Formylbenzoic acid methyl ester, methyl 4-[2- (6-methoxy-2H-chromen-3-yl)propenyl]benzoate is obtained. (EXAMPLE 21)

4-Formylbenzoic acid ethyl ester, ethyl 4-[2-(6-methoxy-2H-chromen-3-yl)propenyl]benzoate is obtained. (EXAMPLE 22)

N TM Ethyl-4-formylbenzamide, N TM ethyl-4-[2-(6-methoxy-2H-chromen-3-yl)propenyl]benzamide is obtained. (EXAMPLE 23)

Ethyl 4-formylphenyl sulfone, ethyl 4-[2-(6-methoxy-2H-chromen-3-yl)propenyl]phenyl sulfone is obtained. (EXAMPLE 24)

Table C shows the data relating to the synthesis of the 4 examples.

Table D shows the physicochemical characteristics of the products.

TABLE C

SYNTHESIS OF EXAMPLES 21 TO 24

| EX N° | R | STEREO-CHEMISTRY | STAGE B Yld | STAGE C Yld (%) | STAGE C M.p. (°C.)* | STAGE D RT (H) | STAGE D Yld (%) |
|---|---|---|---|---|---|---|---|
| 21 | COOCH$_3$ | E | 95 | 77 | 110 | 24 | 27 |
| 22 | COOC$_2$H$_5$ | E | 95 | 77 | 110 | 24 | 42 |
| 23 | CONHC$_2$H$_5$ | E | 95 | 77 | 110 | 18 | 38 |
| 24 | SO$_2$C$_2$H$_5$ | E | 95 | 77 | 110 | 24 | 15 |

RT = Reaction time

TABLE D

PHYSICOCHEMICAL CHARACTERISTICS OF EXAMPLES 21 TO 24

| Ex No | M.p. (°C.) | ELEMENTAL ANALYSIS CALCULATED | FOUND | SPECTROMETRY NUCLEAR MAGNETIC RESONANCE* (δ) ppm |
|---|---|---|---|---|
| 21 | 110° C. | C 74.98 | C 74.44 | 2.10: s, 3H (CH$_3$, ethylenic 3.65 s, 3H, OC$\underline{H_3}$ at 6- |
| | | H 5.99 | H 6.01 | 3.85 s, 3H ester C$\underline{H_3}$ 4.95 s, 2H, C$\underline{H_2}$ (2) |

TABLE D-continued

| | | PHYSICOCHEMICAL CHARACTERISTICS OF EXAMPLES 21 TO 24 | | |
|---|---|---|---|---|
| | M.p. | ELEMENTAL ANALYSIS | | SPECTROMETRY |
| Ex No | (°C.) | CALCULATED | FOUND | NUCLEAR MAGNETIC RESONANCE* (δ) ppm |
| 22 | Oil | C 75.41<br>H 6.33 | C 74.79<br>H 6.37 | 6.40 s ethylenic H<br>6.60–8.20 c, 8H, aromatic and $H_4$, $H_5$, $H_7$, $H_8$<br>1.40, t, 3H $OCH_2$—$\underline{CH}_3$ 2.15: s, 2H, ethylenic $CH_3$<br>3.85 s, 3H, $\underline{OCH}_3$ at 6-position 4.40: q, 2H, $\underline{OCH}_2CH_3$ |
| 23 | 170° C. | C 75.62<br>H 6.63<br>N 4.00 | C 75.59<br>H 6.65<br>N 4.00 | 4.85 s, 2H, $H_2$ at 2-position<br>6.55–8.15 c, 9H, aromatic and $H_4$, $H_5$, $H_8$ ethylenic<br>1.25: t 3H, $NHCH_2\underline{CH}_3$ J=7$H_2$<br>2.10: s, 3H, $CH_3$<br>3.5: 2H $NH\underline{CH}_2CH_3$ J=7$H_2$ |
| 24 | 122° C. | C 68.08<br>H 5.98 | C 67.92<br>H 6.16 | 3.8 s, 3H, $OCH_3$, 5.05: s, 2H, $CH_2$ at 2-position<br>6.40–6.80: c, 6H, ethylenic, NH, $H_4$, $H_5$, $H_7$, $H_8$<br>7.25–7.95: c, 4H aromatic AA'BB'<br>1.30: 3H, t, $SO_2CH_2\underline{CH}_3$, 3.15 q, 2H, $SO_2\underline{CH}_2CH_3$<br>3.85: s, 3H, $OCH_3$ 4.85, s, 2H, $H_2$ at 2-position<br>6.40–8.20: c, 9H, ethylenic and aromatic H | s: singlet;
t: triplet;
q: quartet;
c: complex

EXAMPLE 25: 3-(1-PHENYLPROPEN-2-YL)-7-METHOXY-2H-CHROMENE

STAGE A: 7-METHOXY-3-ACETYL-2H-CHROMENE 1.52 g (10 mmol) of 2-hydroxy-4-methoxybenzaldehyde, 0.66 g (10 mmol) of 3-oxo-1-butene and 0.79 g (10 mmol) of pyridine are added at room temperature and with mechanical stirring to a suspension of 0.14 g (1 mmol) of potassium carbonate in 100 ml of dimethylformamide. The mixture is brought to reflux while magnetic stirring is maintained for 6 hours. The reaction medium is then poured into 200 ml of 0.5 N aqueous sodium hydroxide solution and thereafter extracted three times with 100 ml of diethyl ether. The organic phases are combined, washed twice with 100 ml of saturated aqueous sodium chloride solution and dried. The solvents are evaporated off and the product is purified by chromatography (see Table A1)
Yield: 42%

STAGES B TO D

The procedure is as in Example 1, 3-acetyl-2H-chromene being replaced by 7-methoxy-3-acetyl-2H-chromene. The expected product is obtained.

EXAMPLES 26 TO 28

Using the procedure described in Example 25, by replacing benzaldehyde in stage D by:
4-Formylbenzoic acid methyl ester, methyl 4-[2-(7-methoxy-2H-chromen-3-yl)propenyl]benzoate is obtained. (EXAMPLE 26)
4-Formylbenzoic acid ethyl ester, ethyl 4-[2-(7-methoxy-2H-chromen-3-yl)propenyl]benzoate is obtained. (EXAMPLE 27)
Ethyl 4-formylphenyl sulfone, ethyl 4-[2-(7-methoxy-2H-chromen-3-yl)propenyl]phenyl sulfone is obtained. (EXAMPLE 28)
Table E shows the data relating to the synthesis of these examples.
Table F shows the physicochemical characteristics of these products.

TABLE E

| | | SYNTHESIS OF EXAMPLES 26 TO 28 | | | | |
|---|---|---|---|---|---|---|
| | | STEREO- | STAGE B | STAGE C | | STAGE D |
| EX N° | R | CHEMISTRY | Yld (%) | Yld (%) | M.p. °C. | (H) | Yld (%) |
| 26 | $COOCH_3$ | E | 92 | 95 | 70 | 18 | 48 |
| 27 | $COOC_2H_5$ | E | 92 | 95 | 70 | 45 | 108 |
| 28 | $SO_2C_2H_5$ | E | 92 | 95 | 70 | 04 | 35 |

Using the procedure described in Examples 1 or 2, but replacing benzaldehyde in stage D by:
4-chlorobenzaldehyde, 3-[(4-chlorophenyl)propen-2-yl]-2H-chromene of stereochemistry E +Z (EXAMPLE 29) or E (EXAMPLE 30) is obtained
para-tolualdehyde, 3-[1-(p-tolyl)propen-2-Yl]2H-chromene of stereochemistry E +Z (EXAMPLE 31) or E (EXAMPLE 32) is obtained
para-anisaldehyde, 3-[1-(4-methoxyphenyl)propen-2-yl]-2H-chromene of stereochemistry E +Z (EXAMPLE 33) or E (EXAMPLE 34) is obtained

TABLE F

| | | PHYSICOCHEMICAL CHARACTERISTICS OF EXAMPLES 26 TO 28 | | | |
|---|---|---|---|---|---|
| | M.p. | ELEMENTAL ANALYSIS | | SPECTROMETRY | |
| Ex No | (°C.) | CALCULATED | FOUND | INFRARED (cm$^{-1}$) | NUCLEAR MAGNETIC RESONANCE* (δ) ppm |
| 26 | 143° C. | C 74.98<br>H 5.99 | C 74.88<br>H 6.09 | 1720, 1620, 1120 | 2.10: s, 3H, $CH_3$ ethylenic<br>3.75: s, 3H, $OCH_3$ (7)<br>3.90: s, 3H, ester $OCH_3$; 5.05: b.s. 2H, $H_2$ (2)<br>6.20–8.10: 9H ethylenic and aromatic |

TABLE F-continued

| | M.p. | ELEMENTAL ANALYSIS | | SPECTROMETRY | |
|---|---|---|---|---|---|
| | | PHYSICOCHEMICAL CHARACTERISTICS OF EXAMPLES 26 TO 28 | | | |
| Ex No | (°C.) | CALCULATED | FOUND | INFRARED (cm$^{-1}$) | NUCLEAR MAGNETIC RESONANCE* ($\delta$) ppm |
| 27 | 180° C. | C 75.41 | C 75.25 | | 1.40 t, 3H, OCH$_2$—C$\underline{H}_3$ |
| | | H 6.33 | H 6.10 | | 2.15: c 3H, ethylene CH$_3$ |
| | | | | | 3.85: s, 3H, OCH$_3$ (7) |
| | | | | | 4.45: q, 2H, OC$\underline{H}_2$CH$_3$ |
| | | | | | 5.20: b.s. 2H, H (2); 6.50 b.s. 1H ethylene |
| | | | | | 6.60–8.35 = : complex 8H chromane and benzenic |
| 28 | 156° C. | C 68.15 | C 68.21 | | 1.30 t, 3H, SO$_2$CH$_2$C$\underline{H}_3$ J=7H$_2$ |
| | | H 5.99 | H 6.06 | | 2.15 c, 3H, ethylene CH$_3$ |
| | | | | | 3.15 q, 2H, SO$_2$—C$\underline{H}_2$ J=7H$_2$ |
| | | | | | 3.80 s, 3H, OCH$_3$; 5.10, b.s. 2H, HZ |
| | | | | | 6.40–6.80 c 4H, H$_4$, H$_6$, H$_8$ + ethylenic H |
| | | | | | 6.90–8.10 c, 5H, H$_5$ and Har AA'BB' | s: singlet;
d: doublet;
t: triplet;
q: quartet;
c: complex

EXAMPLE 35: 4-[2 TM (2H TM CHROMEN-3-YL)PROPENYL]-BENZOIC ACID

By alkaline hydrolysis of methyl 4-[2-(2H-chromen-3-yl)propenyl]benzoate in the presence of alcoholic potassium hydroxide, the product of the title is obtained.
Yield: 45%
Melting point: 175° C.

| Percentage composition: | | |
|---|---|---|
| Calculated: | C: 75.22 | H: 5.64 |
| Found: | C: 75.72 | H: 5.63 |

Spectral characteristics Nuclear magnetic resonance $\delta$=2.15 ppm 3H singlet, CH$_3$

PHARMACOLOGICAL STUDY

EXAMPLE 36: INHIBITION OF GROWTH OF L1210 LINE

The growth of this mouse leukemic line is assessed by the capacity of the cells to incorporate tritiated thymidine. The degree of incorporation is measured 48 hours after the introduction of the test compounds into the culture medium.

Table F collates the values for 50% growth inhibition (IC$_{50}$) for each product.

| EX N° | IC$_{50}$ ($\mu$M) 48 hours |
|---|---|
| 1 | <1 |
| 3 | 20 |
| 6 | 25 |
| 8 | 25 |
| 10 | 18 |
| 13 | 3.8 |
| 16 | 3.8 |
| 17 | 7.5 |
| 18 | 6 |
| 24 | 8 |
| Etretinate | 80 |

This study shows that the examples studied have markedly greater activity than that of etretinate.

EXAMPLE 37: STUDY OF THE TOXICITY ON THE HUMERI OF RAT FETUSES OF GESTATIONAL AGE 21 DAYS

The toxicity of retinoids can be evaluated on humeri of rat fetuses of gestational age 21 days.

The toxicity of retinoids can be evaluated on humeri of rat fetuses explanted in vitro as described by KISTLER.

Retinoid activity results in a release of proteoglycans from the bony substance. This release is assessed after 7 days of culture in vitro by assaying the concentration of proteoglycans in the medium, by the method of WITHEMAN (1973).

The compounds of the present invention generally prove 3- to 8-fold less toxic than etretinate. The compound of Example 8 showed a complete absence of toxicity in this test.

EXAMPLE 38: DETECTION OF AN EXCESS-VITAMIN A TYPE TOXICITY IN VIVO

The side effects limiting the use of retinoid agents in human clinical medicine are the appearance of a hypervitaminosis A syndrome. This can be reproduced experimentally in animals.

The selected treatment protocol is a daily injection for five days, repeated a second time after an interval of two days. It is identical to that used by BOLLAG et al (1981). Whereas retinoic acid and etretinate cause a rapid weight loss, the appearance of alopecia and bone weakening, manifestations of their toxicity, compounds of the present invention proved devoid of excess-vitamin A type toxicity: no statistically significant sign in respect of weight, no fracture detectable by radiography and no onset of alopecia were reported following treatment with the compounds of the invention.

EXAMPLE 39: EXAMPLE OF A PHARMACEUTICAL COMPOSITION

Tablet containing a 5 mg dose of 3-(1-phenylpropen-2-yl)-2H-chromene

| Preparation formula for 1,000 tablets | |
|---|---|
| 3-(1-Phenylpropen-2-yl)-2H-chromene | 5 g |
| Wheat starch. | 20 g |
| Corn starch | 20 g |
| Lactose | 75 g |

-continued

| Preparation formula for 1,000 tablets | |
|---|---|
| Magnesium stearate | 2 g |
| Silica | 1 g |
| Hydroxypropylcellulose | 2 g |

We claim:

1. A compound selected from those of the formula (I):

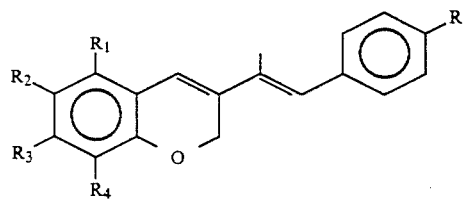

in which:

R denotes a hydrogen atom, a halogen atom or a hydroxy, lower alkyl, lower alkyloxy, carboxyl, (lower alkyloxy)carbonyl, (lower arylalkyloxy)carbonyl, aminocarbonyl, (lower mono- or dialkyl)aminocarbonyl or (lower arylalkyl)aminocarbonyl group, an aminocarbonyl group N-substituted with a heterocyclic radical selected from the group consisting of thiophene, pyrrole, benzothiophene, benzopyrrole, pyridine, pyrimidine, piperidine, morpholine, thiomorpholine, and pyrrolidine, or a thio, (lower alkyl)-thio, or (lower alkyl)sulfonyl group, $R_1$, $R_2$, $R_3$ and $R_4$, which may be identical different, denote a hydrogen atom, a halogen atom or a lower alkyl, lower alkenyl, lower alkyloxy or lower alkenyloxy group, optionally substituted with one or more halogen atoms, or a stereoisomer thereof, and, when R denotes a carboxyl, a salt thereof with a pharmaceutically-acceptable base and, when R contains a basic group, an addition salt thereof when a pharmaceutically-acceptable acid.

2. A compound as claimed in claim 1, in which R denotes an ethoxycarbonyl group.

3. A compound as claimed in claim 1, in which R denotes a methoxycarbonyl group.

4. A compound as claimed in claim 1, in which R denotes a (lower alkyl)sulfonyl group.

5. A compound as claimed in claim 1, in which R denotes a (lower alkyl)aminocarbonyl group.

6. A compound as claimed in claim 1, in which R denotes a hydrogen atom.

7. A compound as claimed in claim 1, in which the configuration is (E),(E).

8. A compound as claimed in claim 1 which is 3(E)-(1-phenylpropen-2(E)yl)-[2H]-chromene.

9. A compound as claimed in claim 1 which is 3-(E)-{1-4-(ethylaminocarbonyl)phenylpropen-2(E)-yl}-(2H)chromene.

10. A compound as claimed in claim 1 which is 3(E)-{1-[4-(ethylsulfonyl)phenylpropen-2(E)-yl}-(2H)chromene.

11. A compound as claimed in claim 1 which is 3-{(E)--[4-(ethylsulfonyl)phenylpropen-2(E)-yl}-6,8-dimethyl-(2H) chromene.

12. A compound as claimed in claim 1 which is 3(E)-{1-4-(ethylsulfonyl)phenyl]propen-2(E)-yl}-6-chloro-8-methyl-(2H) chromene.

13. A pharmaceutical composition, useful in inhibiting the growth of a tumor or neoplasm of the L1210 cell line type or treating a skin disorder of the epithelial type, which is susceptible to treatment with retinoid type chemotherapeutic agents, containing, as active principle, an effective amount of at least one compound as claimed in one of claims 1 to 7 or 8 to 12 inclusive, in combination with one or more pharmaceutically-acceptable, non-toxic, inert vehicles or excipients.

14. Method for inhibiting the growth of a tumor or neo-plasm of the L1210 cell line type or treating a skin disorder of the epithelial type, which is susceptible to treatment with retinoid type chemotherapeutic agents, comprising the step of administering to a subject afflicted with such ailment an amount of at least one compound as claimed in any one of claims 1 to 7 or 8 or 12, inclusive, which is effective for such purpose.

* * * * *

UNITED STATES PATENT AND TRADEMARK OFFICE
CERTIFICATE OF CORRECTION

PATENT NO. : 4,975,455

DATED : Dec. 4, 1990

INVENTOR(S) : Jean-Daniel Brion, Guillaume Le Baut, Patrick Ducrey, Sylvie Piessard-Robert, Claude Cudennec, Genevieve Seurre It is certified that error appears in the above-identified patent and that said Letters Patent is hereby corrected as shown below:

Column 1, line 15; insert a period -- . -- after "benzene".
Column 1, approximately line 42; insert a period -- . -- after "hitherto".
Column 2, line 27/28; "There may be menthiophene, pyrrole," should read -- There may be mentioned, by way of a non-limiting example, pyridine, thiophene, pyrrole, --.
Column 6, approximately line 46; "5,6 TM DIMETHYL-" should read -- 5,6-DIMETHYL- --.
Column 6, approximately line 58; insert a period -- . -- after "nitrogen".
Column 6, approximately line 61; insert a period -- . -- after "minutes".
Column 7, line 6; "hours," should read -- hours' --.
Column 7, line 55; "-4me-" should read -- -4-me- --.
Column 7, line 67; "2 TM butanone." should read -- 2-butanone. --.
Column 13, approximately line 29; "3 TM (1 TM" should read -- 3-(1- --.
Column 13, approximately line 33; "-hydroxy TM 5-" should read -- -hydroxy-5- --.
Column 14, approximately line 42; "N TM Ethyl", first occurrence; should read -- N-Ethyl --.
Column 14, approximately line 42; "N TM ethyl:, second occurrence; should read -- N-ethyl --.
Column 16, approximately line 55; "2-Y1]" should read -- 2-yl] --.
Column 17, line 26; "4-[2 TM (2H TM CHROMEN" should read -- 4-[2-(2H-CHROMEN --.
Column 19, line 44; "when" should read -- with --.
Column 20, line 16; " {1-4-" should read -- {1-[4- --.

UNITED STATES PATENT AND TRADEMARK OFFICE
CERTIFICATE OF CORRECTION

PATENT NO. : 4,975,455            Page 2 of 2

DATED      : Dec. 4, 1990

INVENTOR(S) : Jean-Daniel Brion, Guillaume Le Baut, Patrick Ducrey, Sylvie Piessard-Robert, Claude Cudennec, Genevieve Seurre It is certified that error appears in the above-identified patent and that said Letters Patent is hereby corrected as shown below:

Column 20, line 16; "phenylpropen" should read-- phenyl]propen --.

Column 20, line 19; "phenylpropen" should read -- phenyl]propen--.

Column 20, line 22; "3-{(E)--" should read -- 3(E)- {1 --.

Column 20, line 26; " {1-4-" should read --  {1-[4- --.

Column 20, line 38; "neo-plasm" should read -- neoplasm --.

Signed and Sealed this

Twenty-first Day of July, 1992

Attest:

DOUGLAS B. COMER

Attesting Officer      Acting Commissioner of Patents and Trademarks